United States Patent
Brown et al.

(10) Patent No.: US 6,348,777 B1
(45) Date of Patent: Feb. 19, 2002

(54) POWER MANAGEMENT SYSTEM

(75) Inventors: Houston A. Brown, Poway; John Mossman, La Mesa; George C. Lysy, San Diego, all of CA (US)

(73) Assignee: Alaris Medical Systems, Inc., San Diego, CA (US)

(*) Notice: Subject to any disclaimer, the term of this patent is extended or adjusted under 35 U.S.C. 154(b) by 0 days.

(21) Appl. No.: 09/516,011

(22) Filed: Feb. 29, 2000

(51) Int. Cl.[7] .................................................. H02J 7/00
(52) U.S. Cl. ........................................ 320/160; 320/137
(58) Field of Search ............................... 320/160, 137, 320/150; 307/31, 34, 35, 38, 39, 59, 66

(56) References Cited

U.S. PATENT DOCUMENTS

| | | | |
|---|---|---|---|
| 4,125,895 A | 11/1978 | Buhlmann | 307/31 |
| 4,135,101 A | 1/1979 | Young et al. | 307/39 |
| 4,337,401 A | 6/1982 | Olson | 307/39 |
| 4,349,879 A | 9/1982 | Peddie et al. | 307/35 |
| 4,471,232 A | 9/1984 | Peddie et al. | 307/35 |
| 4,489,386 A | 12/1984 | Breddan | 307/35 |
| 4,549,274 A | 10/1985 | Lerner et al. | 307/39 |
| 4,583,182 A | 4/1986 | Breddan | 307/39 |
| 4,745,299 A * | 5/1988 | Eng et al. | 307/66 |
| 4,819,180 A | 4/1989 | Hedman et al. | 307/35 |
| 4,855,922 A | 8/1989 | Huddleston et al. | 307/38 |
| 4,888,495 A | 12/1989 | Feron et al. | 307/295 |
| 4,889,999 A | 12/1989 | Rowen | 307/31 |
| 4,916,329 A | 4/1990 | Dang et al. | 307/66 |
| 4,935,042 A | 6/1990 | Obelode et al. | 55/484 |
| 5,157,269 A | 10/1992 | Jordan et al. | 307/59 |
| 5,168,170 A | 12/1992 | Hartig | 307/35 |
| 5,170,068 A | 12/1992 | Kwiatkowski et al. | 307/31 |
| 5,237,207 A | 8/1993 | Kwiatkowski et al. | 307/31 |
| 5,256,905 A | 10/1993 | Striek et al. | 307/34 |
| 5,281,859 A | 1/1994 | Crane | 307/139 |
| 5,289,046 A | 2/1994 | Gregorich et al. | 307/66 |
| 5,315,533 A | 5/1994 | Stich et al. | 307/66 |
| 5,317,366 A | 5/1994 | Koshi et al. | 307/31 |
| 5,346,163 A | 9/1994 | Momma et al. | 246/5 |
| 5,424,936 A | 6/1995 | Reddy | 363/97 |
| 5,426,620 A | 6/1995 | Budney | 368/10 |
| 5,465,011 A | 11/1995 | Miller et al. | 307/64 |
| 5,481,140 A | 1/1996 | Maruyama et al. | 307/11 |
| 5,489,836 A | 2/1996 | Yuen | 320/148 |
| 5,510,659 A | 4/1996 | Lewis et al. | 307/11 |
| 5,532,935 A | 7/1996 | Ninomiya et al. | 307/31 |

(List continued on next page.)

OTHER PUBLICATIONS

Intel, "80C51FA/83C51FA Event–Control CHMOS Single–Chip 8–Bit Microcontroller," *Datasheet*, Intel Corporation. Feb. 1995.

Linear Technology. (1994). LTC1325: Microprocessor–Controlled Battery Management System. Database [Online Datasheets] Available Web Site: www.linear.com/cgi–bin/database?function=elementinhtml&filename=DataSheet.html&name=DataSheet&num= 380 Accessed on: Jun. 7, 1999.

Maxim Integrated Products. MAX4173T/F/H Lowe–Cost, SOT23, Voltage–Output, High–Side Current–Sense Amplifier. Database [Online Datasheets] Available Web Site: http://209.1.238.2461stpages/1971.htm Accessed on: May 7, 1999.

Maxim Integrated Products. MAX4172 Low–Cost, Precision, High–Side Current–Sense Amplifier. Database [Online Datasheets] Available Web Site: http://209.1.238.246/1st pages/1654.htm Accessed on: May 7, 1999.

*Primary Examiner*—Peter S. Wong
*Assistant Examiner*—Lawrence Luk
(74) *Attorney, Agent, or Firm*—Pennie & Edmonds LLP

(57) ABSTRACT

In a power supply of a patient care system, a power management system monitors the temperature of an off-line switcher and adjusts the amount of current supplied by the off-line switcher to operate the off-line switcher within a range of temperature and power limits.

32 Claims, 11 Drawing Sheets

U.S. PATENT DOCUMENTS

| | | | |
|---|---|---|---|
| 5,534,734 A | 7/1996 | Pugh et al. | 307/38 |
| 5,543,666 A | 8/1996 | Priesemuth | 307/39 |
| 5,543,667 A | 8/1996 | Shavit et al. | 307/39 |
| 5,570,002 A | 10/1996 | Castleman | 323/283 |
| 5,572,073 A | 11/1996 | Burgess et al. | 307/38 |
| 5,583,417 A | 12/1996 | Yuen | 320/160 |
| 5,615,105 A | 3/1997 | Tofigh et al. | 307/31 |
| 5,624,572 A | 4/1997 | Larson et al. | 210/149 |
| 5,637,933 A | 6/1997 | Rawlings et al. | 307/147 |
| 5,650,939 A | 7/1997 | Yoshida | 307/115 |
| 5,687,052 A | 11/1997 | Bennett | 307/115 |
| 5,687,139 A | 11/1997 | Budney | 368/10 |
| 5,712,795 A | 1/1998 | Layman et al. | 320/160 |
| 5,713,856 A | 2/1998 | Eggers et al. | 604/65 |
| 5,747,973 A | 5/1998 | Robitaille et al. | 323/239 |
| 5,764,034 A * | 6/1998 | Bowman et al. | 320/155 |
| 5,770,895 A | 6/1998 | Kumasaka | 307/32 |
| 5,798,901 A | 8/1998 | Signaigo | 361/64 |
| 5,859,480 A | 1/1999 | Ryu et al. | 307/664 |
| 6,018,228 A * | 1/2000 | Dias et al. | 320/106 |

* cited by examiner

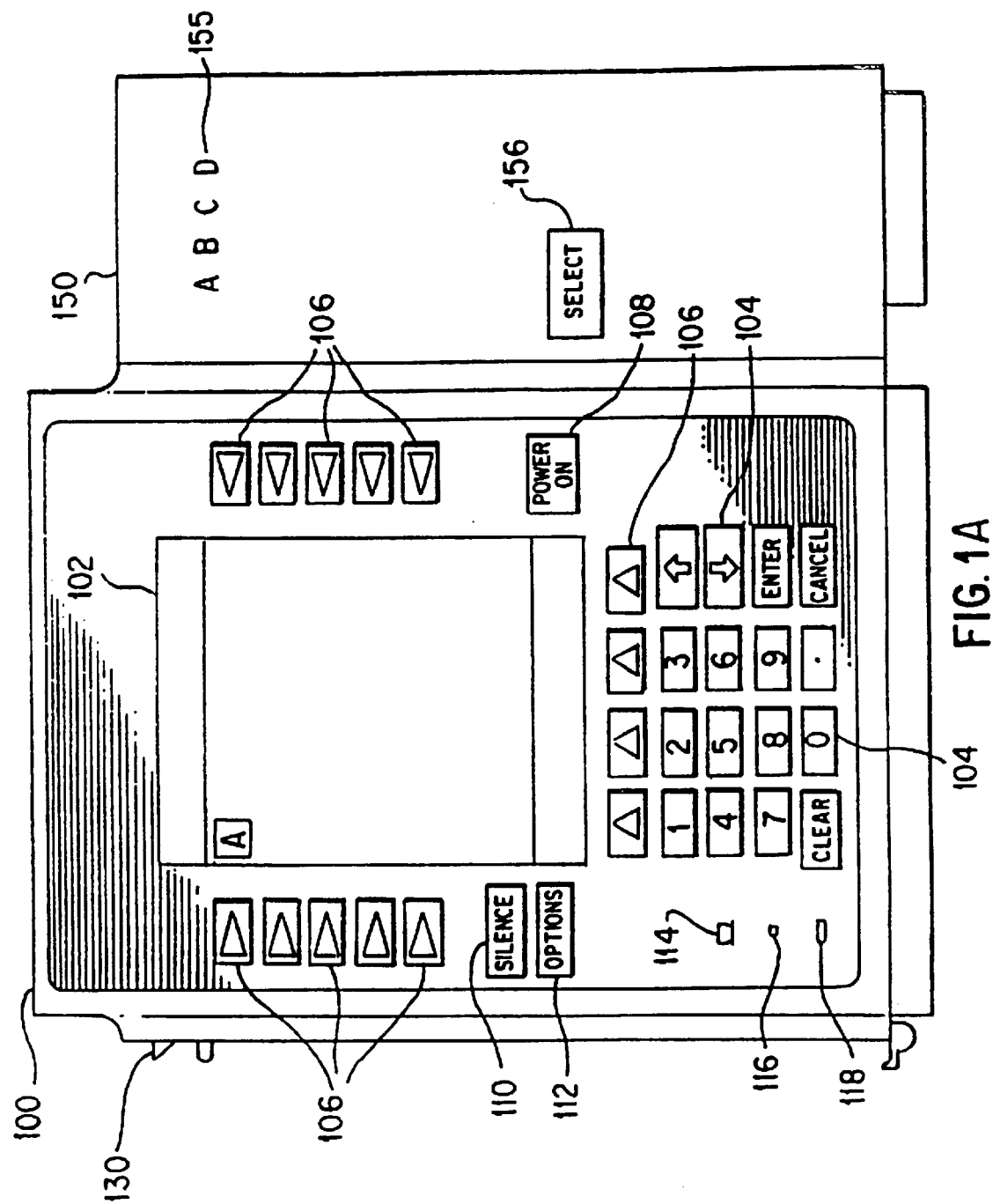

| Temperature | Power |
|---|---|
| 0 | 50 |
| ⋮ | ⋮ |
| 40 | 50 |
| ⋮ | ⋮ |
| 50 | 50 |
| ⋮ | ⋮ |
| 60 | 37 |
| ⋮ | ⋮ |
| 70 | 25 |
| 72 | 0 |
| ⋮ | ⋮ |

252

POWER MANAGEMENT SYSTEM

The present invention relates to a modular, programmable patient care system. Specifically, the present invention relates to an apparatus and method for a power management system for the modular, programmable patient care system.

BACKGROUND OF THE INVENTION

Patient care systems containing multiple infusion pumping units and sensing devices such as blood pressure monitors and pulse oximeters are known in the medical field. For example, U.S. Pat. No. 5,713,856 to Eggers et al. discloses a modular, programmable patient care system comprised of an interface unit removeably attached to a plurality of patient functional units. The interface unit provides an interface between the user and the system, and may be either an advanced interface unit with a high level of interface functionality or a basic interface unit with a lower level of interface functionality. These units may be interchanged so as to provide increased flexibility, safety, and cost-effectiveness to the user. Each interface unit has interface ports for the uploading and downloading of information such as drug libraries, drug infusion profiles, system configuration values, and event history. As patient functional units are added to the interface unit, power requirements increase because each functional unit draws current from the power supply of the interface unit.

The patient care system has a battery backup to supply power when AC power fails or when not connected to AC power, such as when a patient is moved. Typically the battery backup includes rechargeable batteries, such as Nickel-cadmium (NiCd) batteries, to reduce the need to replace batteries and reduce operating cost. After the batteries are used, the batteries need to be recharged. Recharging the batteries draws additional current from the power supply and can be the major load on the power supply.

As the amount of current drawn through the power supply increases, the temperature of various components of the power supply increases. U.S. Pat. No. 5,712,795, to Layman et al., describes a method for monitoring the battery temperature and controlling the charging rate of the battery to extend the service life of the battery. However, this technique does not take into account other important components of the power supply.

For other power supply components, as the temperature increases, the maximum amount of power that can be supplied decreases. Therefore, a method and apparatus are needed to monitor the temperature of certain other components of the power supply and to adjust the amount of power supplied.

SUMMARY OF THE INVENTION

In view of the disadvantages of the related art, it is an object of the present invention to provide a power management system that monitors the temperature of selected components in a modular patient care system and adjusts the amount of power supplied based on the temperature.

In a power supply of a patient care system, a power management system monitors the temperature of an off-line switcher and adjusts the amount of current supplied by the off-line switcher to operate the off-line switcher within a range of temperature and power limits.

In particular, the power supply includes an off-line switcher with an external power input and an internal power output. A first temperature sensor is thermally coupled to the off-line switcher and outputs a first sensed temperature. A voltage sensor is coupled to the internal power output and outputs a sensed output voltage of the off-line switcher. A current sensor is coupled to the internal power output and outputs a sensed output current of the off-line switcher. A battery charger is electrically coupled to the off-line switcher and to a battery. A memory stores a power management procedure. A power supply processor executes the power management procedure. The power management procedure causes the power supply processor to determine an internal power load $P_S$ by multiplying the sensed output voltage $V_S$ by the sensed output current $I_S$, and to determine a power rating $P_{TEMP}$ based on the first sensed temperature. The power management procedure causes the battery charger to reduce a charge rate of the battery based on the power rating $P_{TEMP}$ and the internal power load $P_S$.

In another aspect of the invention, in a patient care system, at least one functional unit is mechanically coupled to an advanced interface unit. The advanced interface unit has a connector electrically coupling the functional unit. The advanced interface unit includes the power supply of the present invention which supplies power to the functional unit via the connector.

In yet another aspect of the invention, a method of managing power in a patient care system is provided.

In another alternate aspect of the invention, a computer program product for managing power in a patient care system is provided. The computer program product is for use in conjunction with a computer system. The computer program product has a computer readable storage medium and a computer program mechanism embedded therein. The computer program mechanism includes a power management procedure and instructions that periodically invoke the power management procedure. The power management procedure causes a battery to charge at a high charge rate, measures a temperature of an internal power source, determines a supplied power supplied by the internal power source at the high charge rate, determines a maximum allowable power for the first temperature, and causes the battery to charge at a low charge rate when the supplied power exceeds the maximum allowable power.

In this way, the power management system ensures that at least one component of the power supply, such as the off-line switcher, operates within temperature and power limits. Because the power management system adjusts the charge rate of the battery to prevent the off-line switcher from overheating and failing, the power management system helps to ensure that higher priority patient care functional units continue to receive power. In addition, the power management system provides a more robust power supply. By operating the off-line switcher within limits, the power supply prolongs the useful life of the off-line switcher and therefore of the power supply.

BRIEF DESCRIPTION OF THE DRAWINGS

Additional objects and features of the invention will be more readily apparent from the following detailed description and appended claims when taken in conjunction with the drawings, in which:

FIG. 1A is a front view of an advanced interface unit connected to a functional unit;

DESCRIPTION OF THE PREFERRED EMBODIMENTS

Figure 1B:
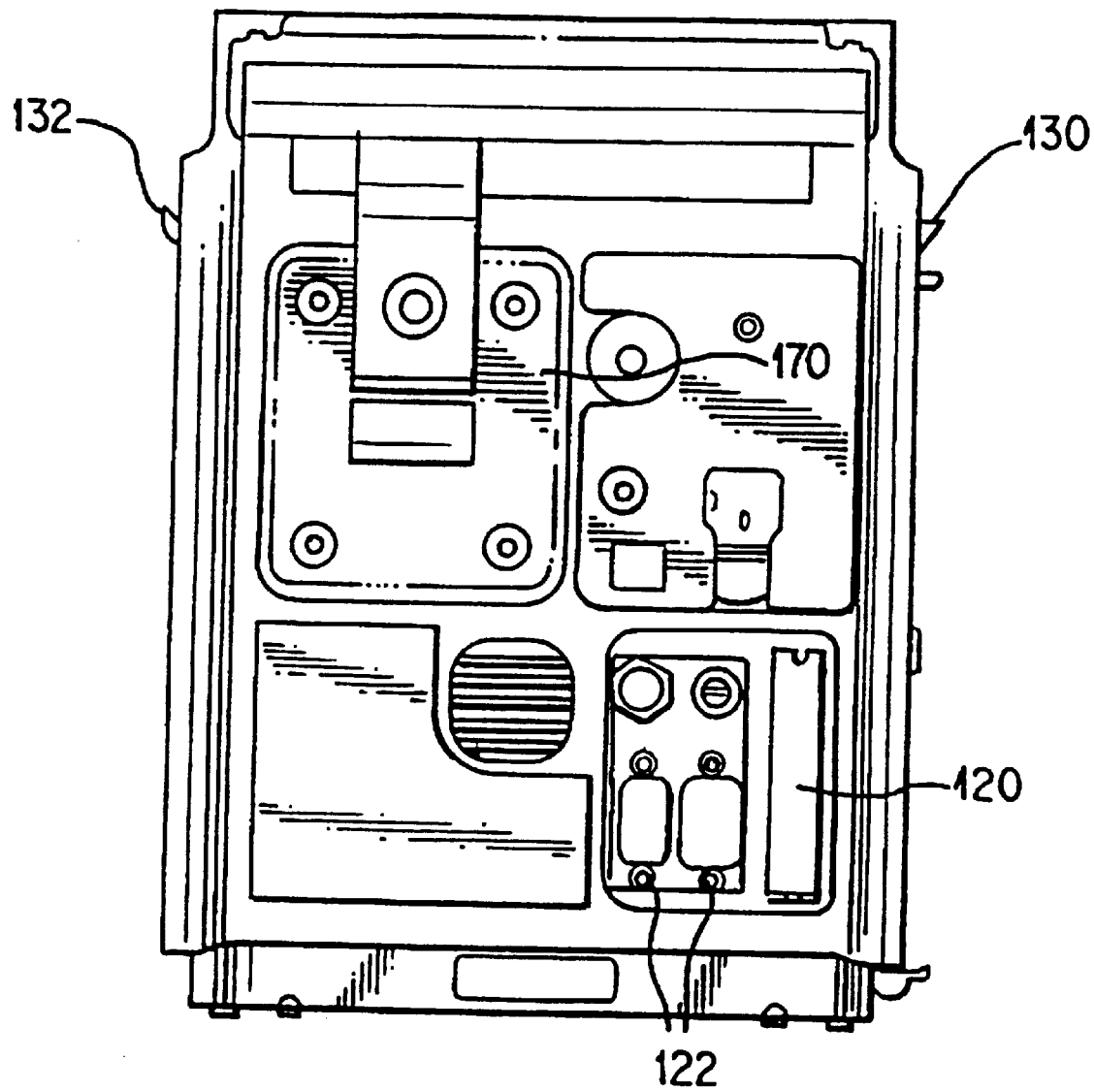
FIG. 1B is a rear view of the advanced interface unit of FIG. 1A.

In FIGS. 1A and 1B a modular, programmable patient care system includes an advanced interface unit 100 and at least one functional unit 150. The advanced interface unit 100 generally performs four functions in the patient care system: providing a physical attachment of the system to structures such as IV poles and bed rails, providing power to the system, providing an interface between the system and external devices, and providing a user interface of the system. The advanced interface unit 100 has an information display 102, which may be any type of display such as a liquid crystal display. The display 102 may be used during setup and operating procedures to facilitate data entry and editing. The display 102 may also be used to display various operating parameters such as volume to be infused (VTBI) for individual functional units 150 which are pumps and current time of day, as well as other prompts, advisories, and alarm conditions. The advanced interface unit 100 contains hardkeys 104 and softkeys 106 for entering data and commands. The numerical hardkeys 104 are used for entering numerical data, while the remainder of the hardkeys 104, as well as the softkeys 106, are used for entering operational commands.

The softkeys 106 may be arranged along the edges of display 102 so as to interact with the display to define the function of a particular softkey 106 at any given time. Therefore, when pressed, a particular softkey 106 will allow for the selection of an option, or an infusion or monitoring parameter, which is displayed on display 102 adjacent to the softkey. As noted, some hardkeys 104 are also used for entering specific operational commands. For example, when the hardkey 108 is pressed, the system changes from standby to operating mode. Alternatively, if hardkey 108 is pressed during a hardware malfunction, it can be used to silence audio alarms and turn off electrical power to the advanced interface unit 100. The SILENCE hardkey 110 may be used to temporarily disable the audio functionality of advanced interface unit 100, while the OPTIONS hardkey 112 allows user access to available system or functional unit options.

The advanced interface unit 100 also has three indicators 114, 116, and 118. The indicator 114 may be used to indicate that the system is communicating with a compatible external computer system. The indicator 116 may be used to indicate that advanced interface unit 100 is connected to and operating with an external power source, and indicator 118 may be used to indicate that the advanced interface unit 100 is operating with the use of an internal power source. The advanced interface unit 100 may also include a tamper-resistant control function (not shown in FIG. 1) which, when enabled, will lock out a predetermined set of controls.

The advanced interface unit 100 preferably also contains at least one external communication interface. A communication interface 120 is located at the rear of advanced interface unit 100. The communication interface 120 is preferably an industry standard personal computer memory card international association (PCMCIA) slot for receiving PCMCIA cards, although one skilled in the art could select from a variety of commercially available communication means. Also located at the rear of advanced interface unit 100 is at least one interface port 122. The interface ports 122 are preferably industry standard RS-232 ports, although again, one skilled in the art could select from a variety of commercially available communication means. It is to be understood that although a preferred embodiment of the invention is described as containing an interface 120 and at least one port 122, any number or combination of communication interfaces and ports could be included in advanced interface unit 100.

The interface 120 and ports 122 illustratively may be used to download drug libraries, drug delivery profiles, and other system configuration values, or may be used to upload event history data from advanced interface unit 100. The interface 120 and ports 122 may also act as an interface to patient monitoring networks and nurse call systems, or as an interface to external equipment such as barcode readers to provide a means of inputting drug and/or patient information from medication or patient records. Performing these functions with the ports 122 and interface 120 will advantageously provide greater functionality and adaptability, cost savings, and a reduction in input errors. Ports 122 and interface 120 may also be supplemented with a Patient Controlled Analgesia (PCA) port (not shown in FIG. 1). The PCA port provides a connection to a remote hand-held "dose request" button which can be used by a patient to request a medication dose during PCA applications.

Located on both sides of advanced interface unit 100 are unit connectors 130 and 132 which are used to attach the functional units 150 which directly contact advanced interface unit 100. These connectors 130 and 132 provide physical support for the attached functional units 150 and provide power and internal communication connections between the advanced interface unit and the functional units. The functional units 150 also contain these unit connectors on either side so that functional units may be connected to the patient care system in a side-by-side manner. A suitable unit connector is described in U.S. Pat. No. 5,601,445, entitled ELECTRICAL AND STRUCTURAL INTERCONNECTOR, incorporated herein by reference.

Finally, advanced interface unit 100 includes a clamp 170 on its rear surface for use in attaching advanced interface unit 100 to a structure such as an IV stand or a hospital bed. The clamp may be any clamp suitable for attaching bedside patient monitoring or infusion apparatus to these structures.

Also shown in FIG. 1A is a functional unit 150. It is to be understood that although only a single functional unit 150 is shown in FIG. 1A, any number of functional units 150 may be connected using the above described unit connectors in any order to either side of advanced interface unit 100. The type and number of functional units attached to advanced interface unit 100 is limited only by the physical and electric ability of the wiring and of the interface unit to handle the desired types and numbers of functional units. Functional unit 150 may be selected from a wide variety of functional units including those for patient therapies and patient monitoring. More specifically, functional unit 150 may be a standard infusion pumping unit, patient controlled analgesia (PCA) pump, syringe pump, pulse oximeter, invasive or non-invasive blood pressure monitor, electrocardiograph, bar code reader, printer, temperature monitor, RF telemetry link, fluid warmer/IV pump, or high rate IV pump (2000+ ml/hr). It is to be understood that this list is for illustrative purposes only and that one skilled in the art could adapt functional unit 150 for other uses.

Each functional unit 150 includes a channel position indicator 155 which identifies the position of the functional unit within a patient care system. As shown by position indicator 155 in FIG. 1A, a system may illustratively contain four channels, A, B, C, and D. If the system contains four functional units, the functional units will each be in one of the four channel positions A, B, C, and D, and the channel position indicator 155 on each individual functional unit will visually indicate the corresponding channel position. Preferably the channel positions are designated A–D, beginning with the first unit on the left. The positions of each functional unit may be interchanged, but the channel locations A–D stay in the same positions relative to advanced interface unit 100. Thus, for example, when four functional units are attached as in FIG. 2, regardless of which unit is placed immediately to the left of advanced interface unit 100, that unit will always indicate channel position B. The functional unit contains certain function specific information which tells advanced interface unit 100 what type of functional unit is at each channel position. Each functional unit 150 also has SELECT key 156, which permits selection of the unit.

Figure 2:
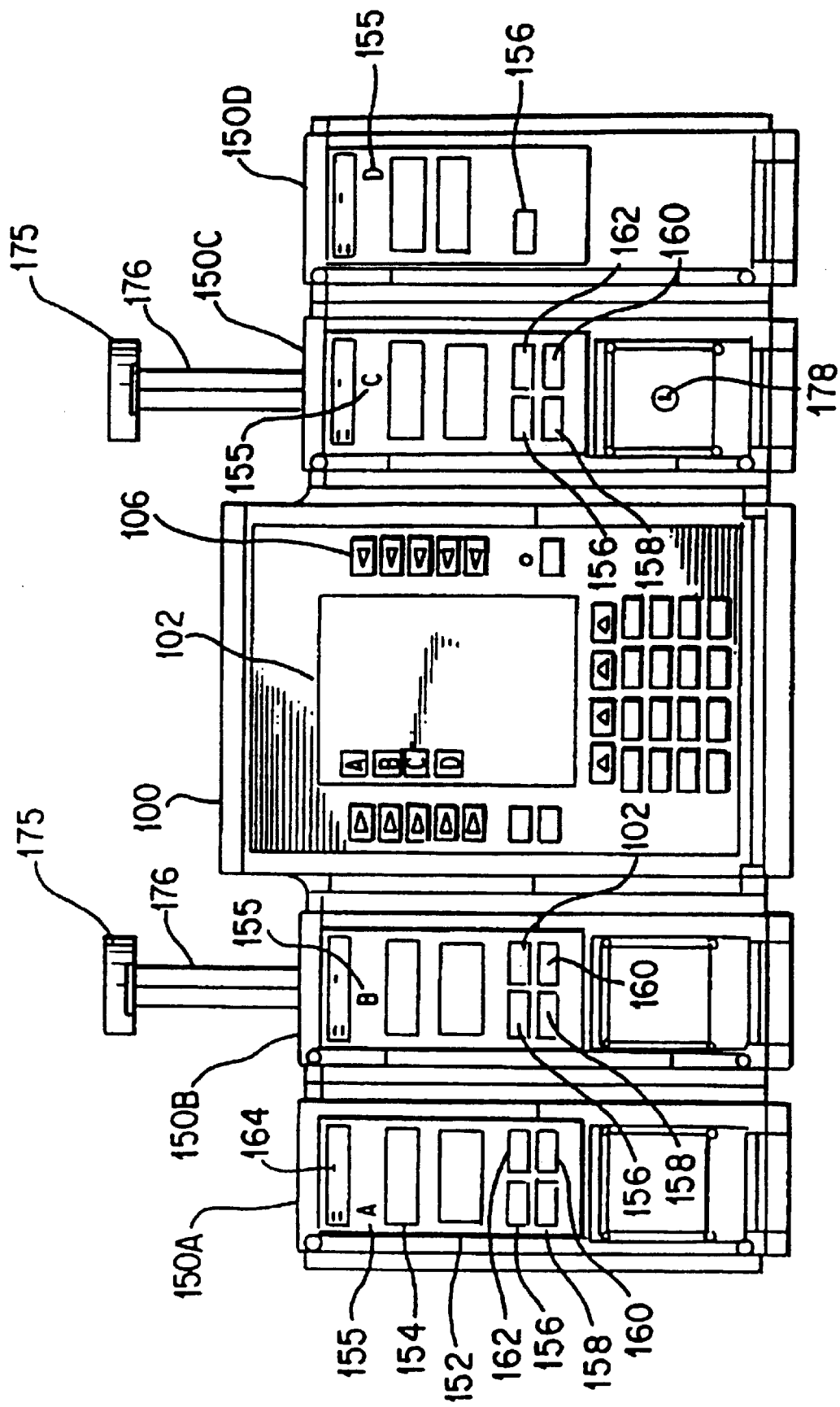
FIG. 2 is a front view of the advanced interface unit of FIG. 1A connected to four functional units.

FIG. 2 illustrates an exemplary system according to the present invention including four different functional units. Infusion pump unit 150A is at position A. Syringe pump 150B is at position B. PCA unit 150C is at position C, and pulse oximeter 150D is at position D. The respective position of each functional unit is indicated on the functional unit at indicator 155. Because four functional units are in use, display 102 on interface unit 100 indicates A through D. In one embodiment, it would be possible to select a functional unit to perform a particular function or procedure through advanced interface unit 100 by depressing the appropriate softkey 106 adjacent to the desired, indicated channel and functional unit. However, in order to provide increased safety, it is preferable that the system be designed such that selection of a particular functional unit requires that SELECT key 156 (see FIG. 1) located on the functional unit be depressed in order to select that functional unit. This requirement will help insure that the proper functional unit is selected, in particular when infusion pump units are used for multiple drug infusions. When the desired functional unit is selected, display 102 of the interface unit is configured so as to act as the user interface for the selected functional unit. More specifically, display 102 is configured in accordance with a function specific domain to provide function specific displays and softkeys as explained in greater detail below.

Infusion pump unit 150A shown in FIG. 2 is a pumping unit for basic fluid infusion. Infusion pump unit 150A includes a system to control the various functions performed by such a pump, which include the control of fluid delivery to the patient and the monitoring of the fluid path for occlusion or air-in-line. Infusion pump unit 150A contains two displays. Rate display 154 may be used to display the actual infusion rate at which the pump is operating. Channel message display 152 may be used to display informational, advisory, alarm, or malfunction messages.

The infusion pump control may also contain hardkeys for data and command entry. Hardkey 156, as mentioned, allows the user to select a channel for infusion parameter entry. Hardkey 158 allows the user to pause an infusion while the infusion is occurring. Hardkey 160 allows the user to resume operation of a previously paused infusion, and hardkey 162, when pressed, stops the infusion occurring on the channel, deselects the channel, and if the functional unit on the channel has been the only functional unit operating, powers off the system.

Infusion pump unit 150A also has indicators 164, which illustratively illuminate when the functional unit is in alarm or infusion complete condition, when the functional unit is programmed for a future start time or has been paused, or when the functional unit is performing an infusion. Other appropriate indicators may be included in other functional units.

Also shown in FIG. 2 is a syringe pump 150B, a PCA unit 150C, and a pulse oximeter 150D. As shown, the syringe pump 150B and the PCA unit 150C each contain a set of hardkeys 156, 158, 160, and 162 like those found on infusion pump unit 150A. The syringe pump 150B and the PCA unit 150C also contain a syringe 176 along with a syringe pusher 175 for manually infusing fluids. The PCA unit 150C includes a door lock 178 for providing security for enclosed narcotics or other matter to be infused. In addition, pump 150B, PCA unit 150C and pulse oximeter 150D each include one or more displays and indicators which may be used to display appropriate information.

As mentioned, located on the sides of the infusion pump unit 150A, as well as all other functional units, are unit connectors (not shown in FIGS. 1A–1B and 2) which are identical to unit connectors 130 and 132 of advanced interface unit 100 disclosed in FIGS. 1A–1B. As mentioned previously, the unit connectors of the functional units 150 are designed to mate with either the connectors on an interface unit or with the connectors from another functional unit. In this manner, multiple functional units 150 may be connected side by side in any order on both sides of advanced interface unit 100. It is to be understood that these unit connectors between advanced interface unit 100 and a functional unit 150 or between two functional units may be made permanent or semi-permanent by some mechanical means such as a screw or a nut and bolt combination. This has the advantage of preventing unintentional or unauthorized detachment of functional units from the system, or to conform to medical institution policy.

A suitable advanced interface unit and functional units are described in U.S. Pat. No. 5,713,856, entitled MODULAR PATIENT CARE SYSTEM, which is incorporated herein by reference in its entirety.

Figure 3:
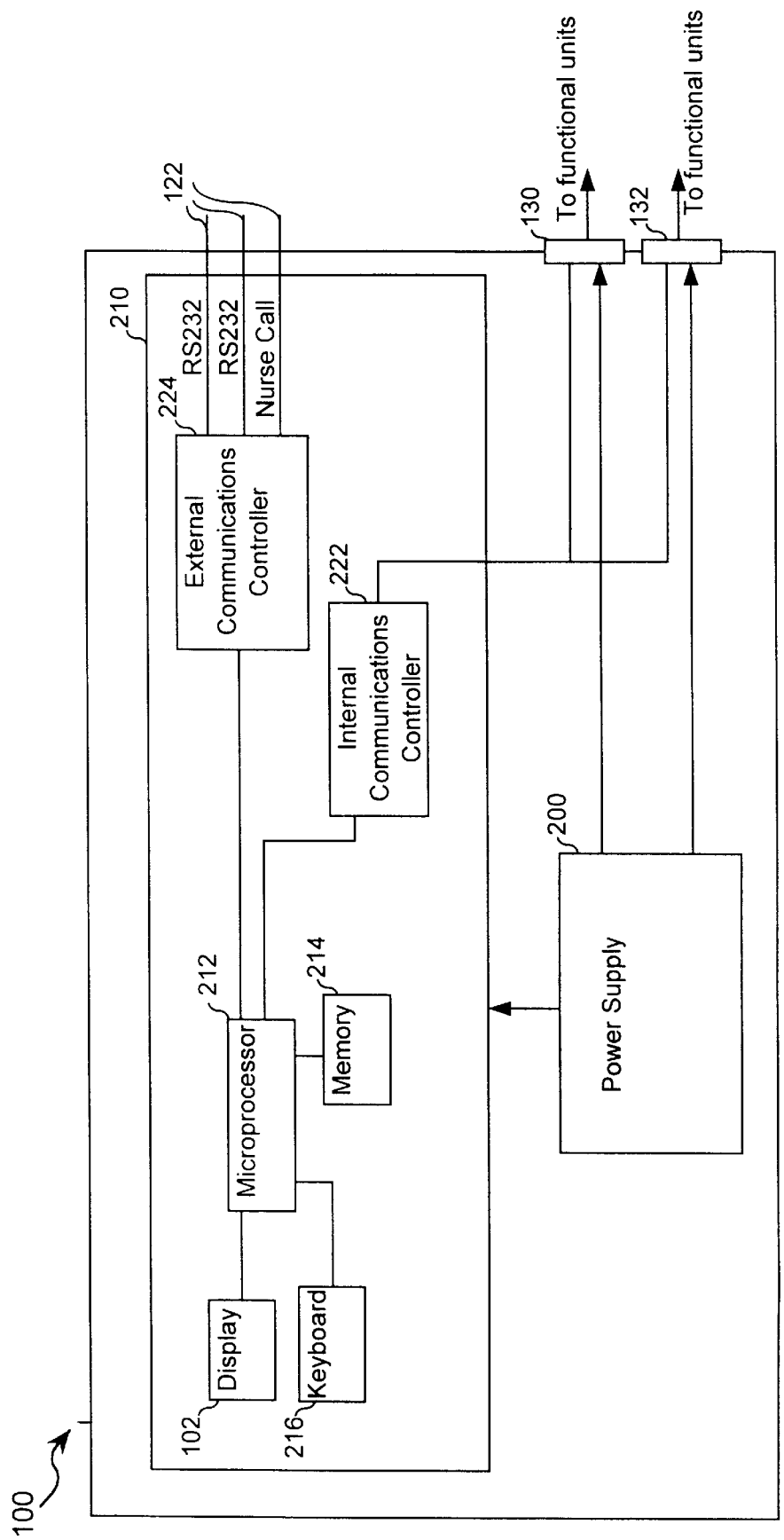
FIG. 3 is a block diagram of the circuitry of the advanced interface unit of FIG. 1A.

As illustrated in FIG. 3, the advanced interface unit 100 has a power supply 200 which supplies DC power to a set of components 210 in the advanced interface unit and to the functional units via the unit connectors 130, 132. A microprocessor 212 and a memory 214 receive and process data and commands from the user, as well as communicate with and control the functional units and other devices external to the system. The memory 214, as well as other memories in the patient care system, discussed below, may be any type of memory or any combination of memories that can be erased and reprogrammed without having to physically remove the memory from the system. Examples of such memories include, but are not limited to, battery-backed random access memory (RAM) and "flash" electronically erasable programmable read only memory (FLASH EEPROM). The advanced interface unit 100 also includes a keyboard 216 with the hardkeys 104 (FIG. 1A) and softkeys 106 (FIG. 1A) and the display 102 as discussed above with respect to FIG. 1A.

The connectors 130 and 132 also provide a data and command interface between the microprocessor 212 and the attached functional units via an internal communication controller 222. An external communications controller 224 controls the command and data flow through RS232 interface ports and the nurse call line 122.

Figure 4:
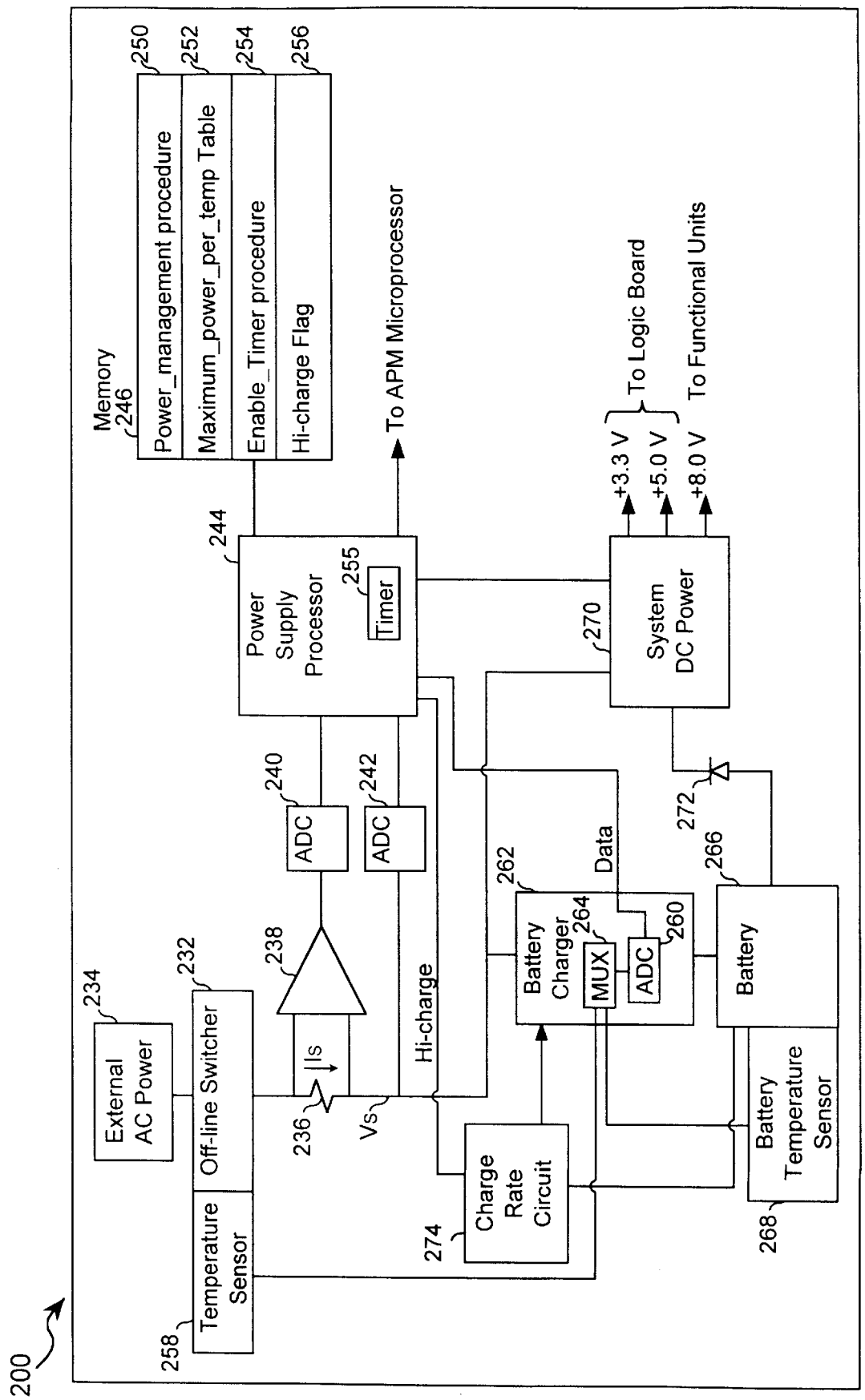
FIG. 4 is a block diagram of a power supply that supplies power to the advanced interface unit and functional units of FIG. 2 and to the circuitry of FIG. 3 according to an embodiment of the invention.

As shown in FIG. 4, the power supply 200 has a power management system which helps ensure that at least one component, such as an off-line switcher 232, operates within temperature and power limits. The power management system monitors the temperature of at least one component of the power supply, and the amount of power supplied by or flowing through that component. The component has a maximum power rating for a range of temperatures. The power management system adjusts the power drawn through the component in accordance with the measured temperature and the measured power to prevent the component from being operated outside of its operational limits and failing. In this way, the system ensures that higher priority patient care functional units continue to receive power. By operating the component within limits, the power supply prolongs the useful life of the component and therefore of the power supply.

In particular, in the power supply 200, the power management system ensures that the off-line switcher 232 operates within temperature and power limits. The off-line switcher 232 converts external AC power 234 to internal DC power. In one embodiment, the off-line switcher 232 receives 120 volts AC and supplies twenty-four volts DC at 2.0 amperes, and has a maximum power output of approximately 50 watts for temperatures ranging from 0° C. to 50° C. For example, a suitable off-line switcher 232 is the GPM50 manufactured by Condor DC Power Supplies Inc.

To measure the current flowing from the off-line switcher 232, a sense resistor 236 is connected in series with the off-line switcher 232. A high side current sense amplifier 238 connects in parallel with the sense resistor 236 and measures the amount of current flowing through the sense resistor 236. The high side current sense amplifier 238 outputs a first voltage level proportional to the measured current. A first analog-to-digital converter (ADC) 240 converts the first voltage level to a digital value that represents the sensed current $I_S$.

A second analog-to-digital converter (ADC) 242 connects to the output of the off-line switcher 232 after the sense resistor 236 and converts the sensed output voltage to a digital voltage level, $V_S$, representing the sensed output voltage.

A power-supply processor 244 is connected to a memory 246 which stores: a Power management procedure 250 that monitors the temperature and power of at least one component of the power supply to operate that component within a range of temperature and power limits;

a Maximum_power_per_temperature (Maximum_power_per_temp) table 252 that stores the range of associated temperature and power limits;

an Enable_Timer procedure 254 that is used in one implementation to cause the power management procedure 250 to be periodically executed using a timer 255; and a Hi-charge flag 256 that is used in an alternate embodiment of the power management procedure to coordinate the adjustment of the battery charge rate based on both (1) the temperature of and the amount of power supplied by the off-line switcher and (2) the temperature of the battery.

In one implementation, power-supply processor 244 may be a DS87C520 microprocessor manufactured by Dallas Semiconductor. The power-supply processor 244 receives the digital values representing the sensed current $I_S$ and the digital sensed output voltage $V_S$. As will be described below, in the power management procedure 250, the power-supply processor 244 uses the sensed current $I_S$ and output voltage $V_S$ to monitor the amount of power output by the off-line switcher 232.

To measure the temperature of the off-line switcher 232, a first temperature sensor 258 is placed adjacent or sufficiently close to the off-line switcher 232 so as to be thermally coupled to the off-line switcher 232. In particular, the first temperature sensor 258 measures the ambient temperature surrounding the off-line switcher 232. In one embodiment, the first temperature sensor 258 is adjacent the off-line switcher 232. In an alternate embodiment, the first temperature sensor 258 is placed at a predetermined fixed distance from the off-line switcher 232 and measures that ambient temperature. The ambient temperature at the predetermined fixed distance is different from the ambient temperature of the off-line switcher 232 and this temperature difference is known. For example, the first temperature sensor 258 is placed about five inches from the off-line switcher 232 and thus the measured ambient temperature is approximately fifteen degrees higher than if the first temperature sensor 258 were placed adjacent the off-line switcher 232. In this example, the power management procedure 250 subtracts the known temperature difference, here fifteen degrees, from the measured ambient temperature. The temperature sensor may be appropriately located by a person of ordinary skill and temperature sensing corrections made as taught herein. The first temperature sensor 258 is a thermistor having a value of 50 K ohm at twenty-five degrees Celsius.

Another analog-to-digital converter (ADC) 260 converts the first temperature signal to a digital first sensed temperature signal TOLS. Preferably, a battery charger 262, such as an LTC 1325 Microprocessor-Controlled Battery Management System manufactured by Linear Technology, Inc., receives the first temperature signal from the first temperature sensor 258, converts the first temperature signal to a digital value using the ADC 260 via a multiplexer 264, and outputs the digital first sensed temperature value TOLS to the power-supply microprocessor 244.

The battery charger 262 controls the charging of the battery 266. The battery 266 provides power to the advanced interface unit and functional units, including the memory 246 and 250 (FIG. 3), when the advanced interface unit is disconnected from the external power source 234, external power is lost or when the off-line switcher 232 fails.

A battery temperature sensor 268 is placed adjacent or sufficiently close to the battery 266 to measure the temperature of the battery 266 and outputs a battery temperature signal. The battery temperature sensor 268 is a thermistor. The analog-to-digital converter 260 converts the battery temperature signal to a digital battery temperature signal.

Preferably, the battery charger 262 also receives the battery temperature signal from the battery temperature sensor 268 and outputs the digital battery temperature value TBAT to the power-supply processor 244.

A DC system power source 270 receives the DC voltage output by the off-line switcher 232 and outputs several voltage levels including +3.3 volts, +5.0 volts and +8.0 volts. The +3.3 and +5.0 volts are supplied to the system 100, while the +8.0 volts is supplied to the functional units via the connectors 130 and 132 (FIG. 1B). A diode 272 couples the voltage output by the off-line switcher 232 to the battery 266 for charging.

To provide multiple charge rates for the battery 266, a charge rate circuit 274 connects to a sense input of the battery charger 262. The battery charger 262 forces the average reference voltage at the sense input to equal a programmable internal reference voltage $V_{DAC}$. The battery charging current will equal the internal reference voltage $V_{DAC}$ divided by the equivalent resistance at the sense input of the charge rate circuit 274.

To provide different charge rates, the charge rate circuit 274 selectively varies the equivalent resistance $R_{SENSE}$ at the sense input of the battery charger 262. The power supply processor 244 outputs a signal called hi-charge to the charge rate circuit 274. When the hi-charge signal is a digital zero, the equivalent resistance $R_{SENSE}$ is such that the battery 266 will be charged at a low charge rate. When the hi-charge signal is a digital one, the equivalent resistance $R_{SENSE}$ is such that the battery 266 will be charged at a high charge rate.

Figure 5:
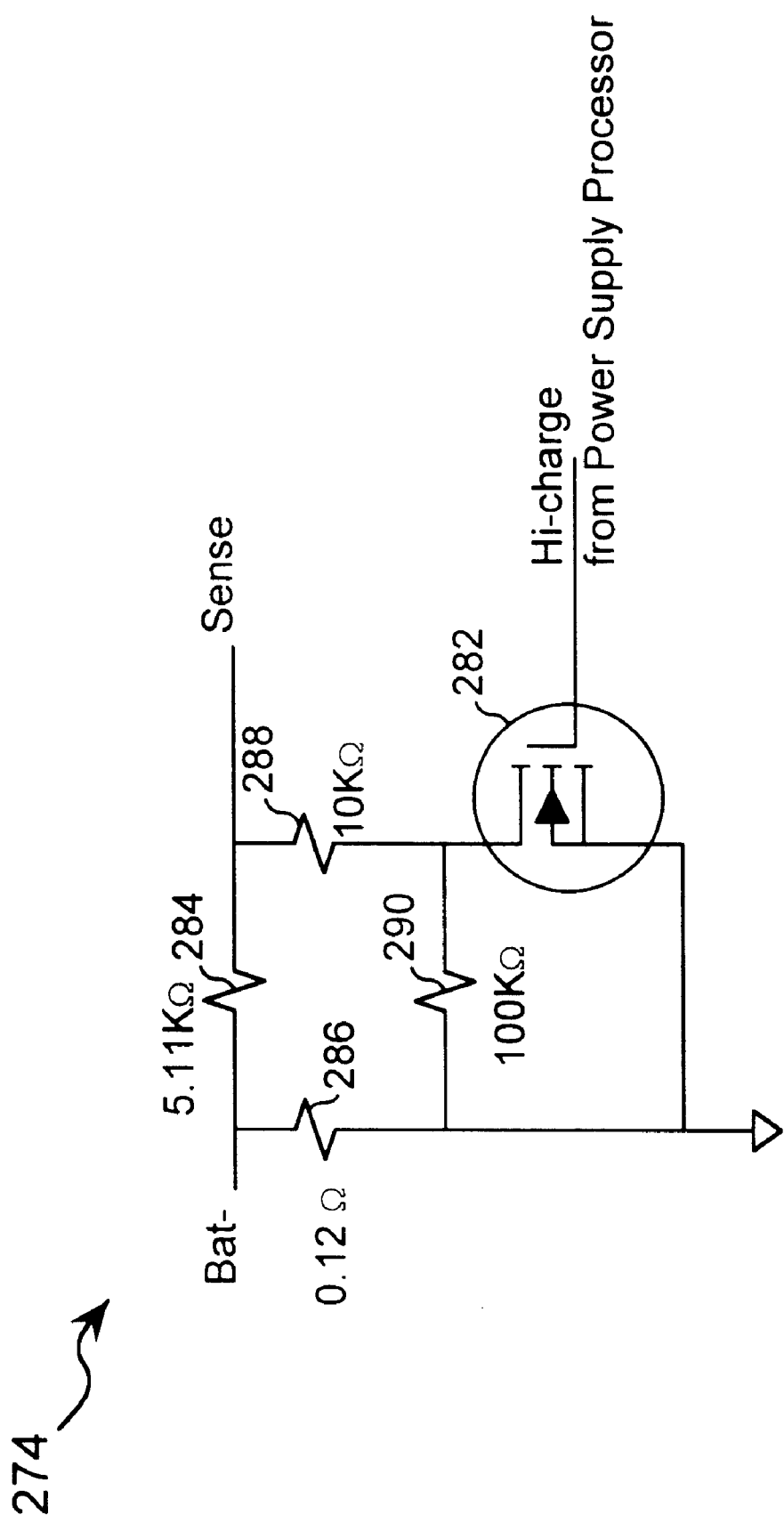
FIG. 5 is a circuit diagram of a charge rate circuit of FIG. 4.

In FIG. 5, in the charge rate circuit 274, the hi-charge signal is connected to the gate of an n-channel transistor 282. The charge rate circuit 274 is a voltage divider. A negative terminal of the battery Bat– is coupled via a first series resistor 284 to the sense input. A second resistor 286 is connected between the negative terminal of the battery and ground. When the hi-charge signal is a digital zero, the n-channel transistor 282 becomes inactive and includes a third resistor 288 and a fourth resistor 290 in the circuit.

In an exemplary embodiment, as shown in FIG. 5, the values of the first, second, third and fourth resistors, 284, 286, 288 and 290, respectively, are chosen such that, at a low charge, the equivalent resistance at the sense input of the battery charger is approximately 0.12 ohm, and the charging current is approximately 1.4 amperes. When the hi-charge signal is a digital one, or high, the transistor 282 becomes active and connects one end of the third resistor 288 to ground, effectively dividing the voltage at the sense input by two-thirds. At the high charge rate, the charging current is approximately 2 amperes.

Figures 6, 7:
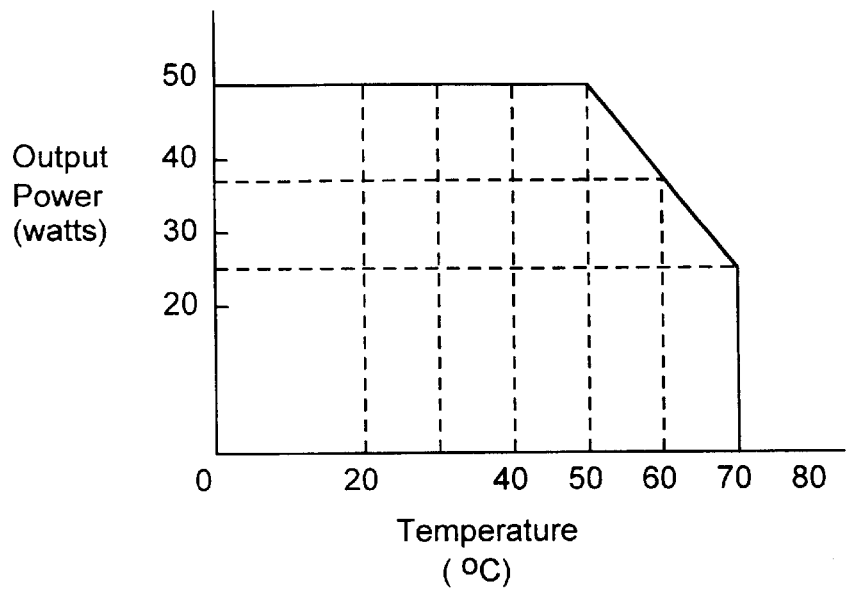
FIG. 6 is a graph of the maximum output power of the off-line switcher versus temperature.
FIG. 7 is an exemplary table storing a maximum power value for temperatures of the graph of FIG. 6 used the by power management procedure of FIG. 4.

Referring to FIG. 6, a graph of the maximum output power of the off-line switcher versus temperature is shown. The maximum amount of power that should be delivered by the off-line switcher 232 declines when the first sensed temperature exceeds a first threshold, and declines linearly with respect to the temperature. In this invention, the power management procedure adjusts the current used to charge the battery to reduce the power flowing from the off-line switcher when the first temperature exceeds a predetermined threshold. At 50° C. the available power declines linearly to one half of a maximum value until the temperature reaches 70° C. Above 70° C. the available power is reduced to zero, however, the power management procedure 250 continues to supply power.

Referring to FIG. 7, an exemplary maximum power per temperature table 252 (FIG. 4) corresponding to the graph of FIG. 6 is shown. In an alternate embodiment, the maximum power per temperature table 252 stores adjusted temperature values that compensate for the temperature difference between the measured ambient temperature and the actual ambient temperature surrounding the off-line switcher, when the first temperature sensor is placed at a predetermined distance from the off-line switcher.

Figure 8:
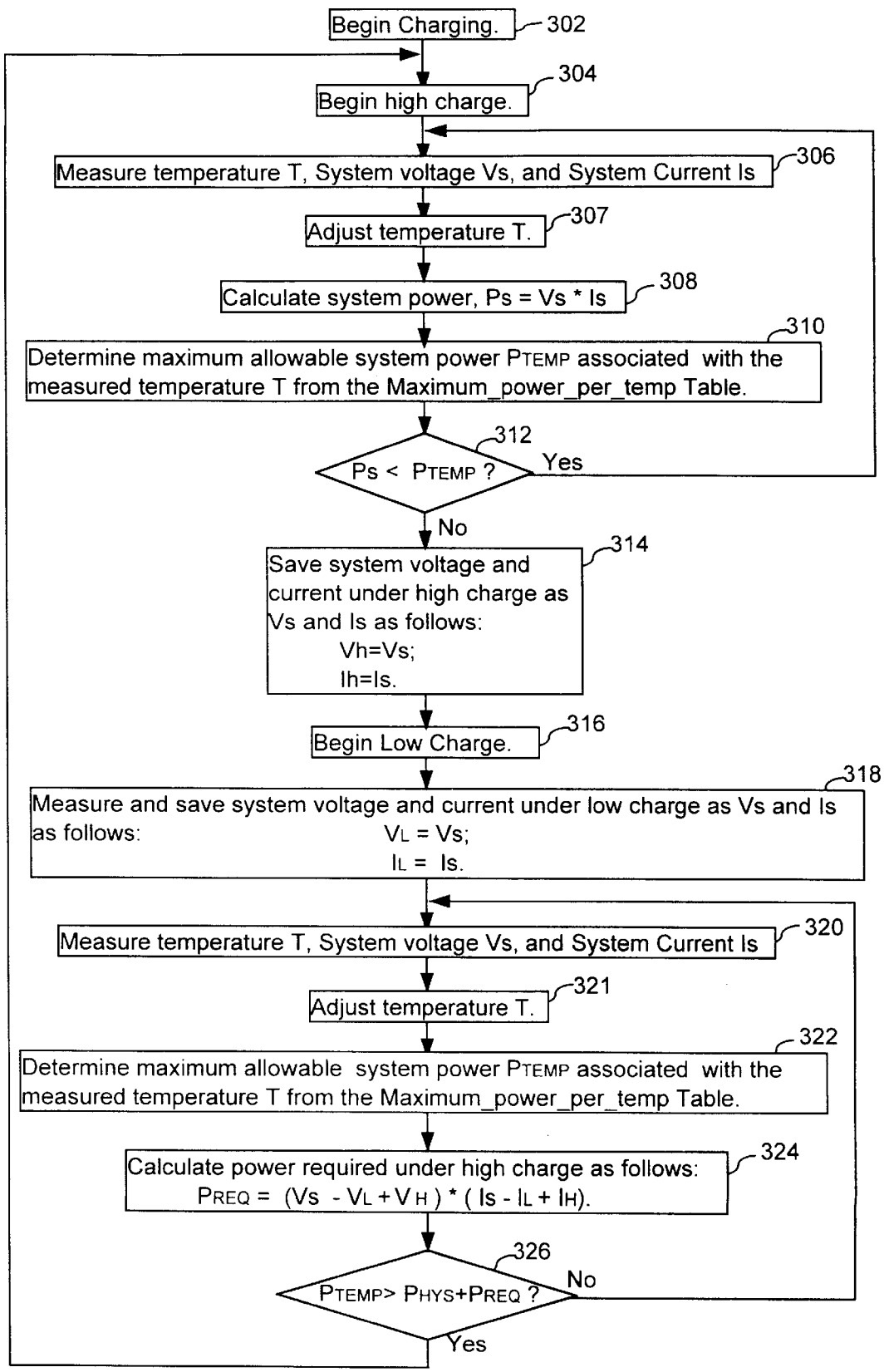
FIG. 8 is a flowchart of an embodiment of power management procedure executed by a power supply processor of the power supply of FIG. 4.

In FIG. 8, a flowchart of the power management procedure 250 executed by the power-supply processor 244 (FIG. 4) is shown. In step 302, the power-supply microprocessor 244 (FIG. 7) causes the battery charger 262 (FIG. 4) to begin charging the battery at a high-charge rate by setting the hi-charge signal to one (step 304). In step 306, the power management procedure 250 measures the first sensed temperature T from the first temperature sensor, and the system voltage $V_S$ and the system current $I_S$ output by the off-line switcher. In step 307, the power management procedure 250 adjusts the first sensed temperature T to compensate for the known temperature difference between the ambient temperature surrounding the off-line switcher and the ambient temperature at the location of the first temperature sensor. As described above, the first temperature sensor may be placed at a predetermined distance from the off-line switcher. A known predetermined temperature differential is subtracted from first sensed temperature T to compensate for the temperature differential. In an alternate embodiment, when the first temperature sensor senses the ambient temperature surrounding the off-line switcher, step 307 is not used. In another alternate embodiment, the temperature values in the maximum power per temperature table are adjusted to compensate for the temperature difference; therefore, the first sensed temperature T is not adjusted. In step 308, the power management procedure 250 calculates the system power $P_S$ by multiplying the voltage $V_S$ by the current Is. In step 310, the power management procedure 250 determines the maximum allowable system power $P_{TEMP}$ associated with the measured first sensed temperature T from the Maximum_power_per_temp table 252 (FIG. 7). In step 312, if the system power $P_S$ is less than maximum allowable system power $P_{TEMP}$, the process repeats at step 306.

If the system power $P_S$ is greater than or equal to the maximum allowable system power $P_{TEMP}$, step 314 saves the system voltage and current under this high charge state by setting a variable $V_H$ to equal $V_S$ and another variable $I_H$ to equal $I_S$.

In step 316, since the off-line switcher is exceeding operational limits, the power management procedure causes the battery charger to charge the battery at a low charge level thereby reducing the amount of current supplied by the off-line switcher by setting the high charge signal to zero. In step 318, the system voltage and current from the low charge state are measured and saved as follows: variable $V_L$ is set equal to $V_S$ and another variable $I_L$ is set equal to $I_S$. The measured voltage and current are saved so to determine and compensate for differences in the amount of power needed by the patient care system. For example, if a functional unit is added, the required system power will increase. If a functional unit is removed, the required system power will decrease. In step 320, after the power supply is in the low charge state, the power management procedure again measures the first sensed temperature T of the off-line switcher, the system voltage $V_S$ and the system current $I_S$. In step 321, the power management procedure adjusts the first sensed temperature T as described above with respect to step 307. Alternately, as described above in step 307, the measured temperature is not adjusted.

In step 322, the power management procedure determines the maximum allowable power $P_{TEMP}$ at the measured first temperature T from the Maximum_power_per_temperature table. In step 324, the power management procedure determines the power required $P_{REQ}$ to return to high charge as follows:

$$P_{REQ}=(V_S-V_L+V_H)*(I_S-I_L+I_H)$$

In step 326, the maximum allowable power $P_{TEMP}$ is compared to $P_{HYS}+P_{REQ}$. When the maximum allowable power $P_{TEMP}$ is less than or equal to $P_{HYS}+P_{REQ}$, the power management procedure repeats at step 320. Otherwise, the power management procedure returns to the high charge state at step 304. Note that a hysteresis value $P_{HYS}$ is added so that the power supply will not switch between the low and high charge states for small power fluctuations.

Figure 9A:
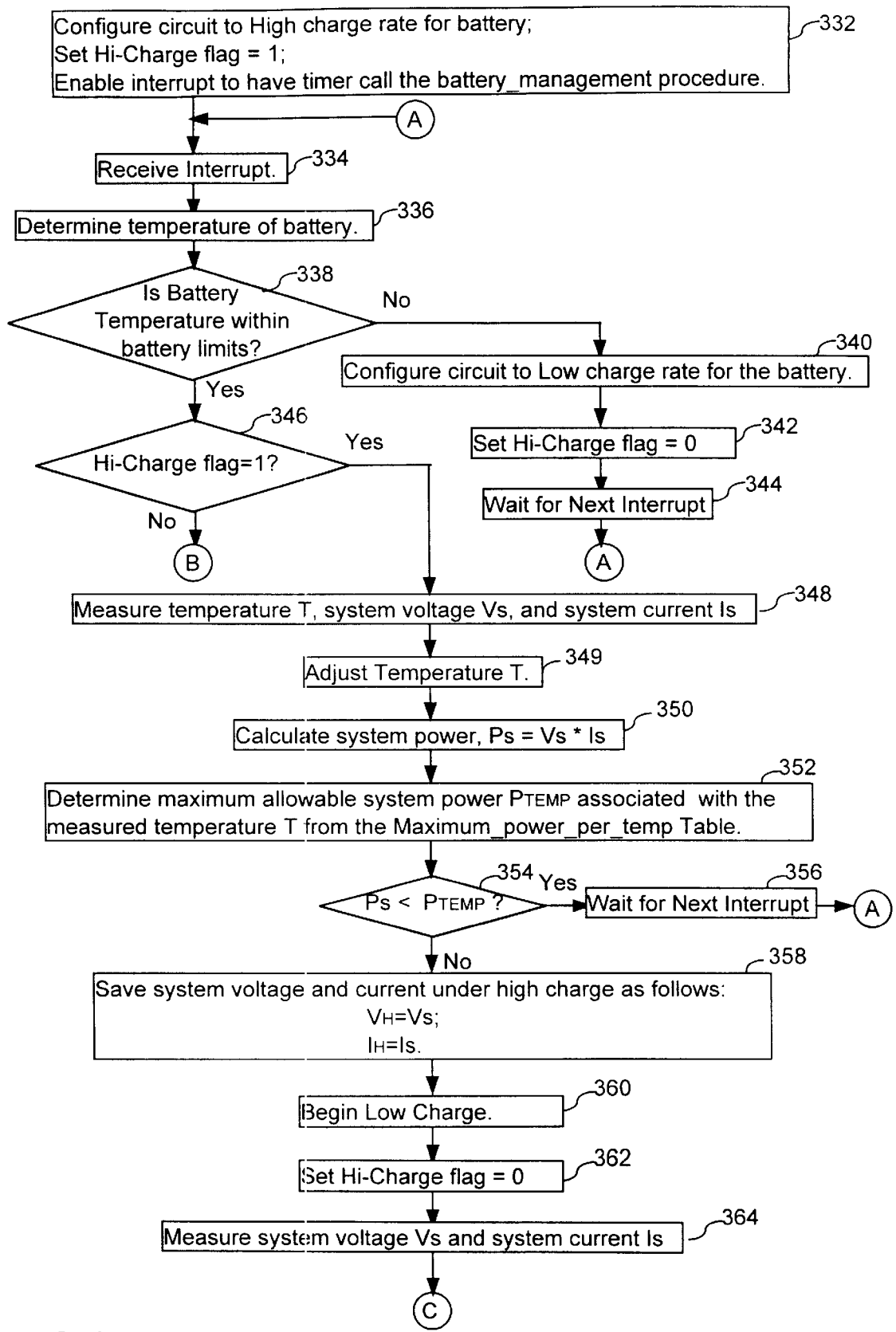
FIGS. 9A, 9B and 9C are flowcharts of an alternate embodiment of the power management procedure which adjusts the power based on the temperature of the off-line switcher while also adjusting the charge rate of the battery based on the battery temperature executed by the power supply processor of FIG. 4.
Figure 9B:
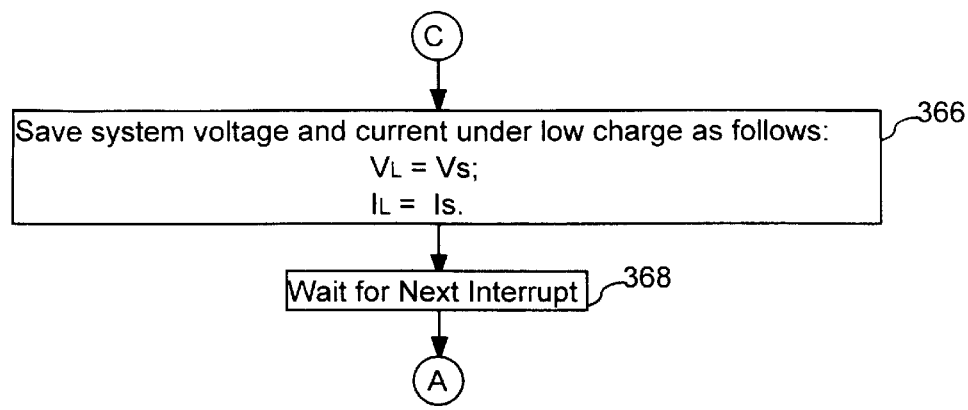
Figure 9C:
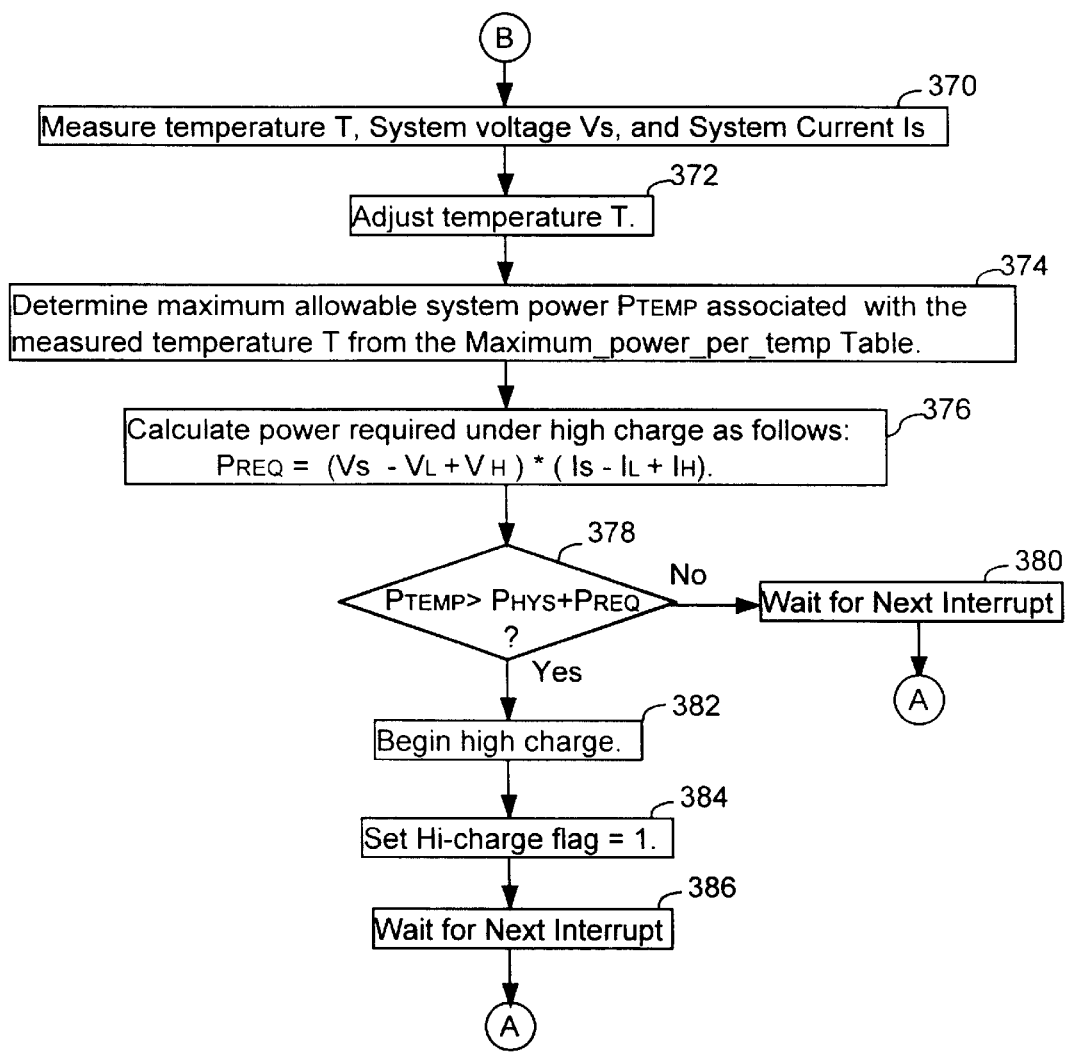

In FIGS. 9A, 9B and 9C, a flowchart of an alternate embodiment of the power management procedure 250 (FIG. 4) is shown. In this embodiment, the enable timer procedure 254 (FIG. 4) causes the power management procedure 250 to be periodically executed at predetermined intervals, such as every second. In this embodiment, the power management procedure 250 coordinates the adjustment of the amount of power supplied by the off-line switcher 232 with the adjustment of the battery charge rate so as to prevent the batteries from overheating.

In step 332, in an enable interrupt procedure 254 (FIG. 4), the power-supply processor 244 (FIG. 4) configures the charge rate circuit 270 (FIG. 4) to the high charge rate by outputting a high charge signal with a value of one, sets a hi-charge flag to one, and enables the timer to generate interrupts to call the power management procedure.

In response to an interrupt (step 334), in step 336, the power-supply processor 244 (FIG. 4) determines the temperature of the battery. Step 338 determines whether the battery temperature is within limits. If not, step 340 configures the charge rate circuit to a low charge rate. In step 342, the hi-charge flag is set equal to zero, and step 344 waits for the next interrupt before proceeding to step 334.

If step 338 determines that the battery temperature is within limits, step 346 determines whether the battery is in the high charge state by determining whether the hi-charge flag is equal to one. If the battery is in the high charge state, in step 348, the power management procedure 250 measures the first sensed temperature T of the off-line switcher, and the voltage $V_S$ and current Is supplied by the off-line switcher. In step 349, the power management procedure 250 adjusts the first sensed temperature T, as described above with respect to step 307 of FIG. 8. In an alternate embodiment, also described above, the first sensed temperature T is not adjusted. In step 350, the power management procedure calculates the system power $P_S$ by multiplying the voltage $V_S$ by the current $I_S$. In step 352, the power management procedure determines the maximum allowable system power $P_{TEMP}$ associated with the measured first sensed temperature T from the Maximum_power_per_temp table.

Step 354 determines whether the system power $P_S$ is less than the maximum allowable system power $P_{TEMP}$. If so, in step 356, the power management procedure ends and waits for the next interrupt. If not, since the batteries are being charged at the high charge rate, in step 358, the measured system voltage $V_S$ and current $I_S$ are saved as $V_H$ and $I_H$, respectively. In step 360, the power management procedure begins a low charge state by outputting a hi-charge signal to the charge rate circuit with a value of zero. In step 362, the power management procedure sets the hi-charge flag equal to zero. In step 364, the power management procedure measures the voltage $V_S$ and the current $I_S$ supplied by the off-line switcher. In FIG. 9B, in step 366, the power management procedure saves the measured system voltage $V_S$ and current $I_S$, as $V_L$ and $I_L$, respectively. In step 368, the power management procedure waits for the next interrupt.

If, in step 346, the hi-charge flag is equal to zero, and the system is in the low charge state, the power management procedure executes a set of steps to determine whether to switch to the high charge state. Referring to FIG. 9C, in step 370, the power management procedure measures the first sensed temperature T of the off-line switcher, and the voltage $V_S$ and the current $I_S$ supplied by the off-line switcher. In step 372, the power management procedure adjusts the measured first sensed temperature T as described above with respect to step 307 of FIG. 8. In an alternate embodiment, the measured temperature T is not adjusted, as described above. In step 374, the power management procedure determines the maximum allowable system power $P_{TEMP}$ associated with the measured temperature from the Maximum_power_per_temp table. In step 376, the power management procedure calculates the required system power to return to the high charge state $P_{REQ}$ as follows:

$$(V_S-V_L+V_H)*(I_S-I_L+I_H).$$

Step 378 determines whether the maximum allowable power $P_{TEMP}$ exceeds the required system power $P_{REQ}$ plus the hysteresis value $P_{HYS}$. If not, in step 380, the charge rate is not changed, the power management procedure and waits for the next interrupt. If so, in step 382, the power management procedure begins a high charge state by outputting a hi-charge signal with a value of one. In step 384, the power management procedure sets the hi-charge flag equal to one. In step 386, the power management procedure waits for the next interrupt.

Figure 10:
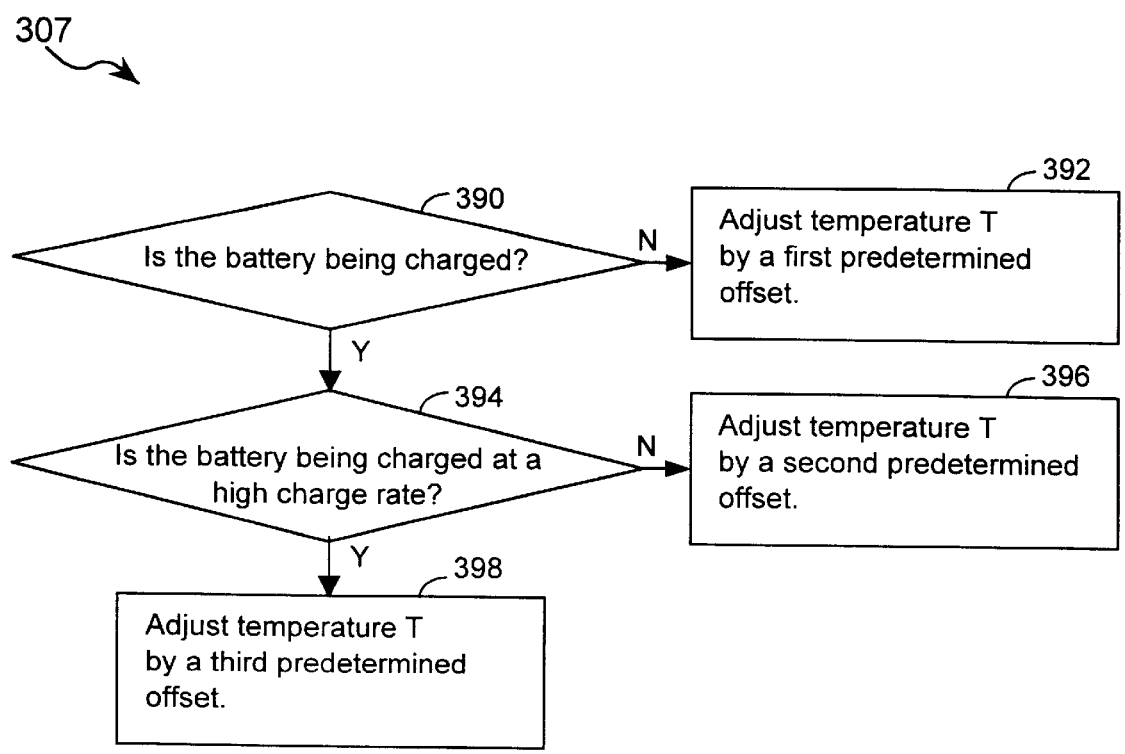
FIG. 10 is a flowchart showing an alternate embodiment of the step of adjusting a sensed temperature of FIGS. 8, 9A and 9C.

FIG. 10 is a flowchart showing an alternate embodiment of step 307 of FIG. 8 that adjusts the first sensed temperature T. Because the battery charger generates different amounts of heat depending on its state, the first sensed temperature varies in accordance with the state of the battery charger. The states of the battery charger include a no-charge state, the low charge state and the high charge state. In the embodiment of FIG. 10, the power managment procedure adjusts the first sensed temperature T by different amounts depending on the state of the battery charger.

In particular, FIG. 10 shows an alternate embodiment of step 307 of FIG. 8; this alternate embodiment may be used in any of the following steps including step 321 (FIG. 8), step 349 (FIG. 9A) and step 372 (FIG. 9C), which adjust the first sensed temperature. In step 390, the power management procedure 250 determines whether the battery is being charged at all. If not, in step 392, the power management procedure adjusts the first sensed temperature T by a first predetermined offset. To adjust the first sensed temperature T, the power management procedure subtracts the first predetermined offset from the first sensed temperature T. In one embodiment, the first predetermined offset is equal to approximately 5° C.

If the battery is being charged, step 394 determines whether the battery is being charged at a high charge rate. If not, the battery is being charged at a low charge rate, and, in step 396 the first sensed temperature T is adjusted by a second predetermined offset. To adjust the first sensed temperature T, the power management procedure subtracts the second predetermined offset from the first sensed temperature T. In one embodiment, the second predetermined offset is equal to approximately 10° C.

If the battery is being at a high charge rate, in step 398, the first sensed temperature T is adjusted by a third predetermined offset. To adjust the first sensed temperature T, the power management procedure subtracts the third predetermined offset from the first sensed temperature T. In one embodiment, the third predetermined offset is equal to approximately 15° C. By adjusting the first sensed temperature in accordance with the state of the battery, the temperature of the off-line switcher is more precisely estimated and the precision of the power management system is improved.

Various embodiments of the invention have been described. The descriptions are intended to be illustrative, not limitative. Thus, it will be apparent to those skilled in the art that modifications may be made to the invention as described without departing from the scope of the claims set out below.

What is claimed is:

1. A power supply for a patient care system, comprising:
   an off-line switcher having an external power input and an internal power output;
   a first temperature sensor outputting a first signal representative of a first sensed temperature adjacent the off-line switcher;
   a voltage sensor outputting a second signal $V_S$ representative of a sensed output voltage of the off-line switcher;
   a current sensor outputting a third signal $I_S$ representative of a sensed output current of the off-line switcher;
   a battery;
   a battery charger communicating with the off-line switcher and the battery to charge the battery at a charge rate;
   a memory storing a power management procedure; and
   processor means communicating with said sensors for varying the charge rate to the battery in accordance with the power management procedure in response to said first, second and third signals.

2. The power supply of claim 1 wherein the processor means further comprises:
   determining an internal power load $P_S$ by multiplying the second signal $V_S$ by the third signal $I_S$; and
   determining a power rating $P_{TEMP}$ based on the first sensed temperature,
   wherein the processor means varies the charge rate in response to said determined internal power load $P_S$ and said determined power rating $P_{TEMP}$.

3. The power supply of claim 1 wherein the power supply processor supplies a charge rate signal indicating the charge rate of the battery, and further comprising:
   a charge rate circuit, responsive to the charge rate signal, coupled to the battery charger, to set the charge rate of the battery, wherein the processor means varies the charge rate using the charge rate signal.

4. The power supply of claim 3 wherein the charge rate circuit includes a voltage divider.

5. The power supply of claim 3 wherein the charge rate signal indicates whether the battery is to be charged at a high charge rate or a low charge rate, and the charge rate circuit sets the charge rate of the battery to the high charge rate or to the low charge rate.

6. The power supply of claim 1 further comprising:
   a battery temperature sensor thermally coupled to the battery and outputting a fourth signal representative of a sensed battery temperature, wherein the power supply processor adjusts the charge rate of the battery in response to the fourth signal.

7. The power supply of claim 1 further comprising:
   a system DC power source, electrically connected to the off-line switcher, electrically connected to the battery, the system DC power source outputting a set of voltages.

8. The power supply of claim 1 wherein the current sensor includes:
   a sense resistor connected in series with the off-line switcher, and a high side current sense amplifier connected across the sense resistor, the high side current sense amplifier outputting the third signal as an analog signal; and
   an analog-to-digital converter that converts the third signal from an analog to a digital third signal for input to the power supply processor.

9. The power supply of claim 1 wherein the battery charger receives the first signal and outputs a digital first signal to the power supply processor.

10. The power supply of claim 1 wherein the power management procedure is periodically executed at predetermined intervals.

11. The power supply of claim 1 wherein the processor means comprises:
    saving the second signal and the third signal at a high charge rate as $V_H$ and $I_H$, respectively, causing the battery charger to reduce the charge rate to a low charge rate, and while in the low charge rate the processor means:
    determines a sensed output voltage $V_L$ and the sensed output current $I_L$,
    determines the power rating $P_{TEMP}$ based on the first signal, and
    causes the battery charger to change to the high charge rate when the power rating $P_{TEMP}$ exceeds $(((V_S-V_L+V_H)*(I_S-I_L+I_H))+P_{HYS})$, where $P_{HYS}$ is a predetermined hysteresis value.

12. The power supply of claim 1 wherein the first temperature sensor is positioned at a predetermined distance from the off-line switcher, and first signal representative of the first sensed temperature includes a temperature offset value in accordance with the predetermined distance.

13. The power supply of claim 12 wherein the temperature offset value is determined in accordance with the charge rate of the battery.

14. A patient care system comprising:
    at least one functional unit; and
    an interface unit adapted to be coupled to and communicate with the at least one functional unit, the advanced interface unit including:
    an off-line switcher having an external power input and an internal power output;
    a first temperature sensor outputting a first signal representative of a first sensed temperature;
    a voltage sensor outputting a second signal $V_S$ representative of a sensed output voltage of the off-line switcher;
    a current sensor outputting a third signal $I_S$ representative of a sensed output current of the off-line switcher;
    a battery to supply a battery voltage;
    a battery charger electrically coupled to the off-line switcher and to the battery charging said battery at a charge rate;
    system DC power means, electrically connected to the off-line switcher and electrically connected to the battery to alternately receive system DC power therefrom, the system DC power means generating a set of voltages, at least one voltage of said set of voltages being supplied to the at least one functional unit;

a memory storing a power management procedure; and processor means communicating with said sensors for varying the charge rate of the battery in accordance with the power management procedure in response to the first, second and third signals.

15. The patient care system of claim 14 wherein the processor means further comprises:

determining an internal power load by multiplying the second signal by the third signal; and determining a power rating based on the first signal, wherein the processor means varies the charge rate in response to said determined internal power load and power rating.

16. The patient care system of claim 14 wherein the processor means supplies a charge rate signal, and further comprising:

a charge rate circuit, responsive to the charge rate signal, coupled to the battery charger to set the charge rate of the battery, wherein the processor means varies the charge rate using the charge rate signal.

17. The patient care system of claim 16 wherein the charge rate circuit includes a voltage divider.

18. The patient care system of claim 16 wherein the charge rate signal indicates whether the battery is to be charged at a high charge rate or a low charge rate, and the charge rate circuit sets the charge rate of the battery to the high charge rate or to the low charge rate.

19. The patient care system of claim 14 further comprising:

a battery temperature sensor thermally coupled to the battery and outputting a fourth signal representative of a sensed battery temperature, wherein the processor means adjusts the charge rate of the battery in response to the fourth signal.

20. The patient care system of claim 14 where in the charge rate is initially a high charge rate, and the processor means comprises:

saving the second signal $V_S$ and the third signal $I_S$ at the high charge rate as $V_H$ and $I_H$, respectively;

causing the battery charger to reduce the charge rate to a low charge rate, and while in the low charge rate the processor means:

determines the sensed output voltage $V_L$ and the sensed output current $I_L$, determines the power rating $P_{TEMP}$ based on the first sensed temperature, and causes the battery charger to change to the high charge rate when the power rating $P_{TEMP}$ exceeds $(((V_s-V_L+V_H)*(I_{S\_IL}+I_H))+P_{HYS})$, where $P_{HYS}$ is a predetermined hysteresis value.

21. The patient care system of claim 14 wherein the first temperature sensor is positioned at a predetermined distance from the off-line switcher, and first signal representative of the first sensed temperature includes a temperature offset value in accordance with the predetermined distance.

22. The patient care system of claim 21 wherein the temperature offset value is determined in accordance with the charge rate of the battery.

23. A method of managing power in a patient care system comprising:

charging a battery at a first charge rate;

measuring a first temperature of an internal power source;

measuring a supplied voltage $V_H$ and a supplied current $I_H$ from the internal power source;

determining a supplied power supplied by the internal power source at the first charge rate;

determining a maximum allowable power $P_{TEMP}$ for the first temperature; and varying the charge rate of the battery when the supplied power exceeds the maximum allowable power $P_{TEMP}$.

24. The method of claim 23 wherein said determining the supplied power includes determining an internal power load $P_S$ by multiplying the sensed output voltage $V_S$ by the sensed output current $I_S$;

wherein said varying varies the charge rate in response to said determined internal power load $P_S$ and power rating $P_{TEMP}$.

25. The method of claim 23 wherein the first charge rate is a high charge rate, and further comprising:

measuring and storing a supplied voltage $V_L$ and a supplied current $I_L$ from the internal power source at the low charge rate;

measuring a operational supplied voltage $V_S$ and a operational supplied current $I_S$ from the internal power source;

measuring a second temperature of the internal power source; and determining the maximum allowable power $P_{TEMP}$ for the second temperature, wherein said varying varies the charge rate by charging at the high charge rate when the maximum allowable power, $P_{TEMP}$, exceeds $((V_S-V_L+V_H)*(I_S-I_{L\_+IH}))+P_{HYS}$, where $P_{HYS}$ is a predetermined power hysteresis value.

26. The method of claim 23 wherein the first temperature sensor is positioned at a predetermined distance from the off-line switcher, and further comprising:

adjusting the first temperature in accordance with the predetermined distance.

27. The method of claim 26 further comprising:

adjusting the first temperature in accordance with the charge rate of the battery.

28. A computer program product for managing power in a patient care system, the computer program product for use in conjunction with a computer system, the computer program product comprising a computer readable storage medium and a computer program mechanism embedded therein, the computer program mechanism comprising:

a power manager that:

causes a battery to charge at a first charge rate, measures a first temperature of an internal power source, determines a supplied power supplied by the internal power source at the first charge rate, determines a maximum allowable power for the first temperature, and varies the charge rate of the battery when the supplied power exceeds the maximum allowable power; and instructions that periodically invoke the power manager.

29. The computer program product of claim 28, the computer program mechanism further comprising:

a battery temperature manager that monitors a battery temperature of a battery and causes the charge rate of the battery to be adjusted based on the battery temperature.

30. The computer program product of claim 28, wherein the first charge rate is a high charge rate, and the power manager further includes instructions that:

measure and store a supplied voltage $V_L$ and a supplied current $I_L$ from the internal power source at a low charge rate;

measure an operational supplied voltage $V_S$ and an operational supplied current $I_S$ from the internal power source;

measure a second temperature of the internal power source; and determine the maximum allowable power $P_{TEMP}$ for the second temperature;

wherein the charge rate is varied when the maximum allowable power $P_{TEMP}$ exceeds $((V_S-V_L+V_H)*(I_S-I_L+I_H))+P_{HYS}$, where $P_{HYS}$ is a predetermined power hysteresis value.

31. The computer program product of claim 28 wherein the first temperature sensor is positioned at a predetermined distance from the off-line switcher, and the power manager further includes instructions that:

adjust the first temperature in accordance with the predetermined distance.

32. The computer program product of claim 31 wherein the power manager further includes instructions that adjust the first temperature in accordance with a charge rate of the battery.

* * * * *